United States Patent [19]

Werner

[11] Patent Number: 5,419,319
[45] Date of Patent: May 30, 1995

[54] VARIABLE POSITION ENDOTRACHEAL TUBE HOLDER

[76] Inventor: Philip J. Werner, HC #1 Box 194E, Brodheadsville, Pa. 18322

[21] Appl. No.: 224,772

[22] Filed: Apr. 8, 1994

[51] Int. Cl.$^6$ .............................................. A61M 16/04
[52] U.S. Cl. ...................... 128/207.17; 128/200.26; 128/207.14; 128/DIG. 26; 604/174
[58] Field of Search ............... 128/207.17, DIG. 26, 128/911, 912, 207.14, 200.24, 200.26; 604/174, 177, 178, 179, 250

[56] References Cited

U.S. PATENT DOCUMENTS

| | | |
|---|---|---|
| 2,735,432 | 2/1956 | Hudson . |
| 3,713,448 | 1/1973 | Arrott . |
| 3,802,431 | 4/1974 | Farr . |
| 3,946,742 | 3/1976 | Eross .................. 128/207.17 |
| 3,987,798 | 10/1976 | McGinnis . |
| 4,223,671 | 9/1980 | Muto . |
| 4,249,529 | 2/1981 | Nestor et al. . |
| 4,270,529 | 6/1981 | Muto . |
| 4,331,143 | 5/1982 | Foster .................. 128/207.17 |
| 4,483,337 | 11/1984 | Clair . |
| 4,744,358 | 5/1988 | McGinnis . |
| 4,906,234 | 3/1990 | Voychehovski . |
| 5,009,227 | 4/1991 | Nieuwstad . |
| 5,123,410 | 6/1992 | Greene et al. . |
| 5,345,931 | 9/1994 | Battaglia, Jr. ............. 128/DIG. 26 |

FOREIGN PATENT DOCUMENTS 2244924  12/1991  United Kingdom ........... 128/207.17

*Primary Examiner*—Edgar S. Burr
*Assistant Examiner*—William J. Deane, Jr.
*Attorney, Agent, or Firm*—Shoemaker and Mattare Ltd.

[57] ABSTRACT

A variable position endotracheal tube holder includes a face piece having an arcuate transverse portion adapted to pass between the nose and upper lip of the patient, and a pair of downwardly extending wings at either end of the transverse portion. The lateral portion of the face piece has upper and lower flanges protruding away from the patient's face, and defining a groove or way which receives and retains a movable support for holding the endotracheal tube. The support includes a slider which can be locked in various positions along the groove, and an integral tube hanger bracket extending downward to the tube.

10 Claims, 2 Drawing Sheets

VARIABLE POSITION ENDOTRACHEAL TUBE HOLDER

BACKGROUND OF THE INVENTION

This invention relates generally to medical equipment and particularly to a variable position endotracheal tube holder.

During various medical procedures and conditions, a tube may be inserted through the mouth, and into the trachea of a patient. The purpose of such intubation may be to ensure proper ventilation, to administer medication, or for other reasons. Similarly, tubes may be placed into the esophagus, or into the nose. In any case, where the patient is to remain intubated for a period of time, it is common to anchor the tube with a clamping fixture worn on the head or adhered to the face of the patient. It is often important that the tube be movable laterally within the mouth, for example when other devices or tubes have to be placed in the mouth, or to enable a practitioner to view the throat. Periodic tube movement, for example every eight hours, is a requirement during long-term intubation.

A number of prior inventors have provided endotracheal tube holders which permit lateral movement of the tube, with respect to a fixed face plate. Some known devices, however, have a disadvantage of covering the mouth, essentially. See, for example, U.S. Pat. No. 4,223,671, which allows for lateral movement of the tube. Plates which block the mouth limit viewing of the mouth and throat by medical personnel.

Another disadvantage of many prior devices is their difficulty of installation. It would be better to have a tube holder whose components could be easily snapped together, when needed.

SUMMARY OF THE INVENTION

An object of the invention is to anchor an endotracheal tube within the mouth opening, without actually blocking the opening.

Another object of the invention is improve oral access.

A further object is to facilitate lateral tube movement by medical personnel, while positively preventing unintended movement.

A related object is to prevent oral injury to an intubated patient.

These and other objects are attained by a variable position endotracheal tube holder including a face piece having an arcuate transverse portion adapted to pass between the nose and upper lip of the patient and a pair of downwardly extending wings at either end of the transverse portion. The wings have slots for receiving harness straps that pass around the head to secure the face piece. The lateral portion of the face piece has upper and lower flanges protruding away from the patient's face, and defining a way which receives and retains a movable support for holding the endotracheal tube.

"Way", is used herein in the mechanical engineering sense, to mean a groove in a fixed part defining a path along which another component can slide.

The support includes an arcuate slider that can slide in the way of the face piece. Two downwardly-biased barbed feet engage detents in the bottom of the groove to hold the slider in a chosen position. Broad tabs extend forward from the feet so that the barbs can be manually released. Protruding from the front of the slider is a hanger bracker having a short horizontal upper leg, a long vertical lower leg, and a tube engaging member at the bottom of the lower leg. The tube engaging member has a concave lower surface, to conform to the shape of the tube. In a preferred embodiment, the tube engaging member has a portion extending into the mouth, to act as a bite block, while in another embodiment, the tube engaging surface is an obliquely extending element useful for holding a nasal cannula.

An advantage of the invention is that the face plate can be applied in a code situation; later, if need be, a tube can be easily inserted through the face plate.

BRIEF DESCRIPTION OF THE DRAWINGS

In the accompanying drawings.

DESCRIPTION OF THE PREFERRED EMBODIMENT

Figure 1:
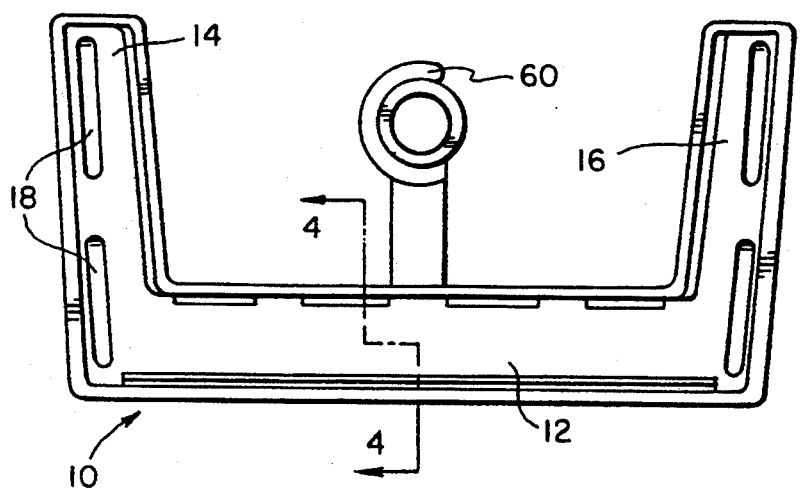
FIG. 1 is a rear elevation of a variable position endotracheal tube holder embodying the invention.
Figure 2:
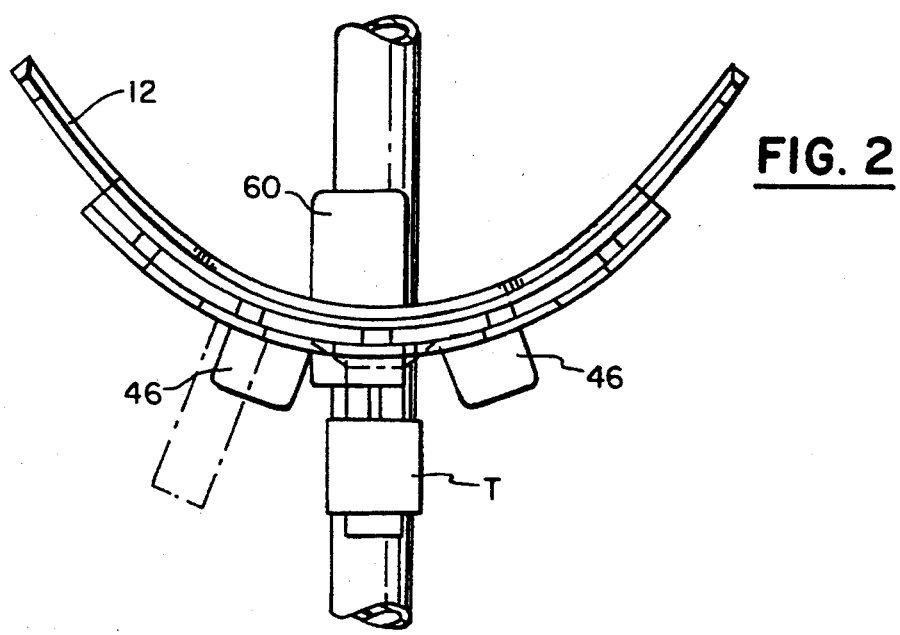
FIG. 2 is a top view thereof.
Figure 3:
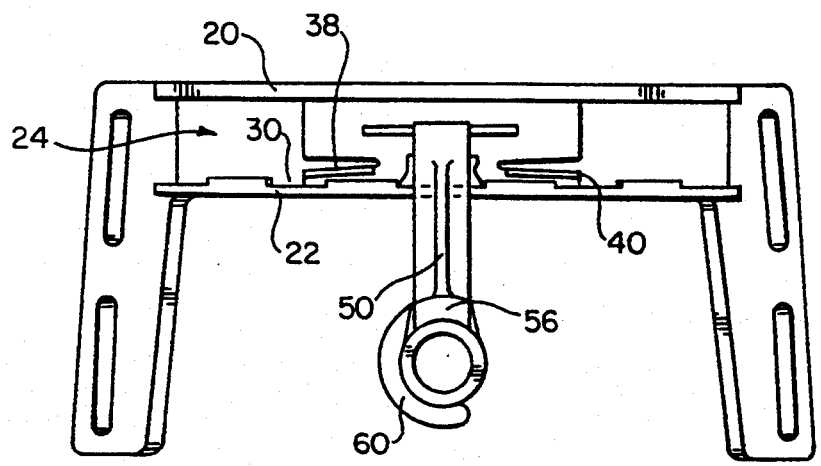
FIG. 3 is a front elevation thereof.
Figure 4:
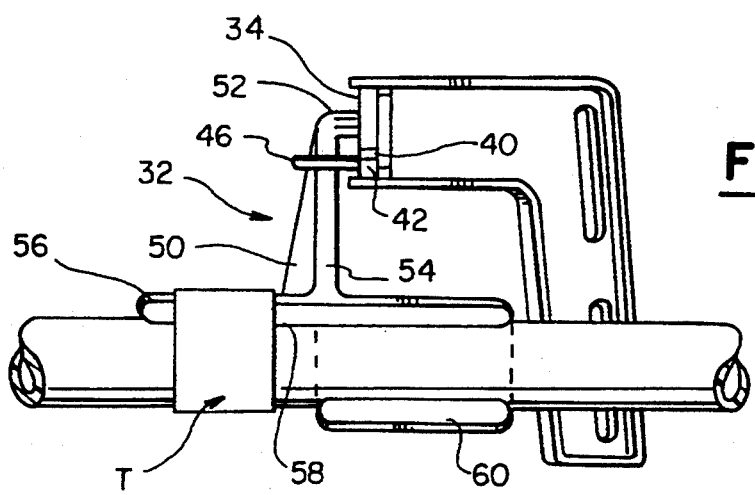
FIG. 4 is a sectional view taken on the vertical plane of symmetry 4—4 in FIG. 2.

As shown in FIGS. 1-3, a variable position endotracheal tube holder embodying the invention includes a face piece 10 having an arcuate laterally extending main portion 12 adapted to pass between the nose and upper lip of the patient, and a pair of downwardly extending wings 14,16 at either end of the transverse portion. The wings have slots 18 for receiving harness straps (not shown) that pass around the head to secure the face piece. The harness may be provided with a placard for posting of medical information such as date of intubation, tube size, tube depth, etc.

The main portion 12 of the face piece has a pair of spaced flanges 20,22 protruding away from the patient's face, and defining a way 24 which receives and retains a movable support for holding the endotracheal tube. The flanges have respective lips 26,28 facing one another. Each has a forwardly facing beveled edge, which allows a slide member described below to be pushed into the way from the front. The lower lip is castellated, having intermittent portions removed, leaving gaps 30.

The support 32 includes an arcuate slider 34 that is inserted into the way 24, and can slide lengthwise in it. The rear vertical surfaces of the lips 26,28 retain the slider. The lower portion of the slide comprises two downwardly-biased splayed feet 38,40, each being longer that the gaps, so it is always retained in the way by the lower lip, regardless of the slider's lateral position. The free height of the slider is somewhat greater than that of the way, so that the feet are bent slightly during deformation. A spring force results. The outer ends of the feet are downwardly facing triangular barbs 42, that engage within detents or holes 44 in the bottom edge of the way to hold the slider in a chosen position. The outer edge of each barb is an oblique surface. Broad tabs 46 extend forward from the feet so that the barbs can be manually released by first lifting the tabs, to overcome the spring force normally keeping the barbs seated in the detents.

Protruding from the front of the slider is a hanger bracket 50 from which the tube is suspended. The bracket has a short horizontal upper leg 52, a long vertical lower leg 54 depending from the forward end of the horizontal leg, and a tube engaging pad 56 at the bottom of the lower leg. The pad has a concave lower surface 58, conforming to the shape of the tube. In the preferred embodiment (FIGS. 1–4), the tube engaging pad has a portion 60 extending into the patient's mouth, acting as a bite block.

Figure 5:
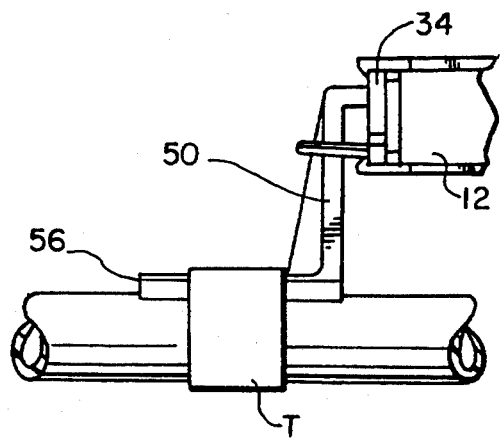
FIG. 5 is a view, like FIG. 4, showing a first modified form of the invention.
Figure 6:
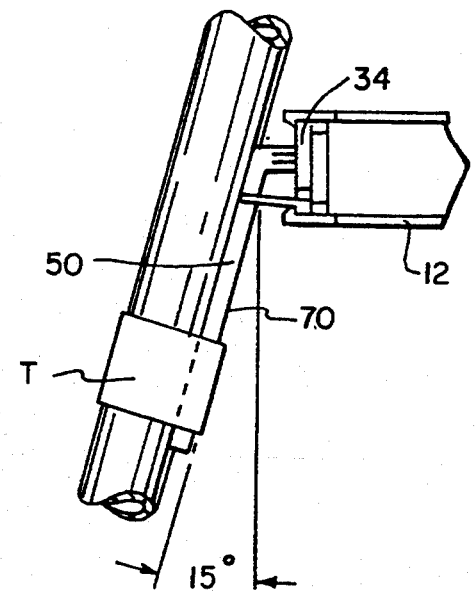
FIG. 6 is a view, also like FIG. 4, of a second modified form of the invention.

In the modified form of the invention illustrated in FIG. 5, the bit block is omitted entirely. And in the embodiment of FIG. 6, which is designed for use with a nasal cannula, it is formed on an obliquely extending element 70. The length of the element 70 makes an angle of about 15° with the vertical, so that it is aligned with the nostrils.

In use, one secures the face piece to the patient's head with the bands mentioned previously, so that its main portion lies between the patient's nose and mouth, and the wings rest against the cheeks. The movable support 32 will probably have already been inserted into the way; if not, the slider may pushed into the way from the front—it snaps in and then cannot be removed—and adjusted laterally to a desired position. The tube is inserted laterally into the bite block from one side (in the cases of FIG. 4), and the endotracheal (or nasal, in the case of FIG. 6) tube is then secured by wrapping a length of tape around the tube and the pad.

Once set up, the tube holder supports the tube reliably, with a minimum of obstruction around the mouth. While accidental movement is prevented by the barbs, the tube can easily be moved left and right by medical attendants, without disturbing the face piece itself.

The components of the device are preferably injection molded from a polymer, such as a polycarbonate, which is medically acceptable for this use. The choice of particular materials is considered a matter of ordinary skill in the field of medical apparatus design.

As mentioned, the device may be used for holding tubing other than endotracheal tubes, and therefore the claims below are not limited to a particular use.

In this document, terms indicative of orientation (e.g., front, back, vertical, horizontal, etc.) are included to clarify the description; however, such terms are not meant to be legally limiting, since the device will be equally useful in any orientation. The terms used describe the approximate orientation that would result, were the patient sitting or standing at attention.

Since the invention is subject to modifications and variations, it is intended that the foregoing description and the accompanying drawings shall be interpreted as illustrative of only one form of the invention, whose scope is to be measured by the following claims.

I claim:

1. A variable position endotracheal tube holder comprising a face piece having a main portion adapted to be placed between the mouth and nose of the patient, upper and lower flanges protruding forward from the main portion of the face piece, said flanges defining therebetween a way in the front surface of the main portion of the face piece, said way extending lengthwise of the main portion, said flanges further having respective upper and lower lips and a tube support comprising a slider retained by said lips for sliding movement within said way, and a hanger bracket whose upper end is connected to the slider, and whose lower end has a pad for engaging a tube passing into the mouth, whereby the tube can be secured to the tube hanger.

2. The invention of claim 1, wherein both the face piece and the slider are arcuate, so as to conform to the contour of the patient's face.

3. The invention of claim 1, wherein the face piece further comprises a pair of wings, one at either end of the main portion of the face piece, said wings having slots for receiving retaining bands to be passed around the head in order to secure the face piece.

4. The invention of claim 1, wherein no portion of the tube holder, other than said tube hanger, passes in front of the mouth of the patient.

5. The invention of claim 1, wherein said slider has means for latching the slider at one of plural positions along the length of said way.

6. The invention of claim 5, wherein the way has plural detents formed along one edge thereof, and the slider has a pair of feet, biased toward said detents, each foot having a barb adapted to seat in said detents, to prevent unintended movement of the slider.

7. The invention of claim 6, wherein each foot has a broad tab affixed to it and protruding forward from the foot, so that one can easily release the barbs from the detents in order to move the tube hanger laterally.

8. The invention of claim 1, wherein the slider further comprises a hanger bracket extending from a forward surface of the slider, said hanger bracket having a downward depending portion terminating at a pad against which the tube may be secured.

9. The invention of claim 8, further comprising a mouthpiece extending rearward from said pad, said mouthpiece being semi-circular in cross-section so that the tube can be inserted into it from one side.

10. The invention of claim 8, wherein the downward depending leg extends along a line oblique to vertical, so that a nasal cannula can be affixed to it.

* * * * *